United States Patent
Tordini et al.

(10) Patent No.: US 11,124,370 B2
(45) Date of Patent: Sep. 21, 2021

(54) UNIT TO FEED COMPONENTS IN AN AUTOMATIC MANUFACTURING MACHINE

(71) Applicant: GDM S.p.A., Bologna (IT)

(72) Inventors: Federico Tordini, Pedrengo (IT); Massimo Pallavera, Soresina (IT); Marco Rosani, Vailate (IT); Matteo Piantoni, Albino (IT)

(73) Assignee: GDM S.p.A., Bologna (IT)

( * ) Notice: Subject to any disclaimer, the term of this patent is extended or adjusted under 35 U.S.C. 154(b) by 0 days.

(21) Appl. No.: 15/733,461

(22) PCT Filed: Jan. 31, 2019

(86) PCT No.: PCT/IB2019/050775
§ 371 (c)(1),
(2) Date: Jul. 31, 2020

(87) PCT Pub. No.: WO2019/150295
PCT Pub. Date: Aug. 8, 2019

(65) Prior Publication Data
US 2021/0101761 A1    Apr. 8, 2021

(30) Foreign Application Priority Data
Jan. 31, 2018    (IT) .................. 102018000002270

(51) Int. Cl.
*B65G 47/91*    (2006.01)
*A61F 13/15*    (2006.01)
(Continued)

(52) U.S. Cl.
CPC ...... *B65G 47/918* (2013.01); *A61F 13/15764* (2013.01); *B65G 54/02* (2013.01);
(Continued)

(58) Field of Classification Search
CPC ... B65B 51/30; B65B 35/10; A61F 13/15764; B65H 20/00; B65H 35/08; B65G 47/244; B65G 54/02; B65G 47/918; B65G 47/848
(Continued)

(56) References Cited

U.S. PATENT DOCUMENTS 5,025,910 A    6/1991   Lasure et al.
6,876,896 B1*  4/2005   Ortiz .................. B29C 66/8351
                                                          700/112
(Continued)

FOREIGN PATENT DOCUMENTS

DE           2806058 A1    8/1979
DE       102010027925 A1   10/2011
(Continued)

OTHER PUBLICATIONS

International Search Report and Written Opinion, corresponding International Application No. PCT/IB2019/050775, dated Jul. 24, 2019.
(Continued)

*Primary Examiner* — James R Bidwell
(74) *Attorney, Agent, or Firm* — Marshall, Gerstein & Borun LLP

(57) ABSTRACT

A feeding unit to feed a component in an automatic manufacturing machine; has: at least one holding head designed to receive and hold the component; a closed curved guide arranged in a fixed position along an application path; an equipment supporting the holding head and provided with at least one slide coupled to the guide by a plurality of wheels; a linear electric motor, and a movable slider electro-magnetically coupled to the stator and is rigidly connected to the slide. The guide has, on the surface in contact with the wheels, a first transverse profile having a concavity or a convexity; the wheels have, on the surface in contact with (Continued)

the guide, a second transverse profile, which has a convexity or a concavity, and generates, with the first profile, a shape coupling between the guide and the wheels, which forbids a transverse movement of the slide relative to the guide.

10 Claims, 11 Drawing Sheets

(51) Int. Cl.
    *B65G 54/02*     (2006.01)
    *B65H 20/00*     (2006.01)
    *B65H 35/08*     (2006.01)

(52) U.S. Cl.
    CPC ............. *B65H 20/00* (2013.01); *B65H 35/08* (2013.01); *B65H 2701/1924* (2013.01)

(58) Field of Classification Search
    USPC ............................................ 198/471.1, 689.1
    See application file for complete search history.

(56) References Cited

U.S. PATENT DOCUMENTS

| | | | |
|---|---|---|---|
| 9,008,831 B1 * | 4/2015 | Jacobs | B65G 43/08 |
| | | | 700/217 |
| 10,919,705 B2 * | 2/2021 | Papsdorf | B65G 43/08 |
| 2010/0219044 A1 * | 9/2010 | Thiel | G01R 31/2893 |
| | | | 198/471.1 |
| 2013/0270066 A1 | 10/2013 | Papsdorf et al. | |
| 2016/0207720 A1 | 7/2016 | Hanisch et al. | |
| 2016/0257089 A1 | 9/2016 | Deering | |
| 2019/0100389 A1 | 4/2019 | Neubauer | |

FOREIGN PATENT DOCUMENTS

| | | | |
|---|---|---|---|
| EP | 1162162 A1 | 12/2001 | |
| EP | 3067172 A1 | 9/2016 | |
| EP | 3038959 B1 | 11/2017 | |
| WO | WO-88/05416 A1 | 7/1988 | |
| WO | WO-00/64753 A1 | 11/2000 | |
| WO | WO-2016/162850 A1 | 10/2016 | |
| WO | WO-2017/108423 A1 | 6/2017 | |
| WO | WO-2017/158572 A1 | 9/2017 | |

OTHER PUBLICATIONS

International Search Report and Written Opinion, corresponding International Application No. PCT/IB2019/050780, dated Apr. 9, 2019.

International Search Report and Written Opinion, corresponding International Application No. PCT/IB2019/050783, dated Apr. 9, 2019.

International Preliminary Report on Patentability, corresponding International Application No. PCT/IB2019/050783, dated Jan. 15, 2020.

* cited by examiner

UNIT TO FEED COMPONENTS IN AN AUTOMATIC MANUFACTURING MACHINE

CROSS-REFERENCE TO RELATED APPLICATION

This application is the U.S. national phase of International Patent Application No. PCT/IB2019/050775 filed Jan. 31, 2019, which claims the benefit of priority from Italian Patent Application No. 102018000002270 filed on Jan. 31, 2018, the respective disclosures of which are each incorporated herein by reference in their entireties.

TECHNICAL FIELD

The invention relates to a unit to feed components in an automatic manufacturing machine.

This invention finds advantageous application in the feeding of components in an automatic manufacturing machine to manufacture hygiene absorbent articles, to which explicit reference will be made in the description below without loosing in generality.

PRIOR ART

A known manufacturing machine to manufacture hygiene absorbent articles comprises a moving line for a continuous band of impermeable material (e.g. polyethylene), along which there are arranged a plurality of operating units, which feed the band, in a continuous manner, with the base components (such as, for example, the absorbent padding or a layer of nonwoven fabric permeable to liquids) and the accessories (such as, for example, elastic bands, faeces barriers and side wings), which define the absorbent article.

Each operating unit comprises a feeding unit provided with a main drum (usually hinged so as to rotate, with a continuous motion, around a central rotation axis), which supports a plurality of sucking holding heads, each designed to receive a corresponding component, which is separated from a continuous band by means of a crosswise cut. In an input station, each sucking holding head receives a corresponding component, which is still part of the continuous band (namely, is the final end of the continuous band) and is subsequently separated from the continuous band by means of a crosswise cut made by a cutting device arranged downstream of the input station. Downstream of the cutting device, each head can by rotated by 90° so as to change the orientation of the component. Finally, in an output station, each sucking holding head releases the corresponding component.

In known feeding units, in order to convey the sucking holding heads, it is possible to use a transport system with directly operated linear electric motors, as described in patent application WO2017158572A1.

The transport system with linear electric motors described in patent application WO2017158572A1 has, for each sucking holding head, one single slide, which supports the holding head as it slides along a central guide. In particular, each slide is coupled to the guide thanks to four pair of idle wheels arranged perpendicularly to one another so as to ensure a crosswise containment of the slide relative to the guide and allow the slide to only slide along the guide. The pairs of wheels generally must be arranged at a close distance, so as to allow the slide to also slide along the parts of the guide having a reduced bending radius, thus covering sharp bends. As a consequence, the aforesaid slides usually are small-sized.

However, this configuration cannot stand fast production rates, as the structure of the slide, which usually is asymmetric, causes a quick wear of part of the wheels of the slide, thus generating a greater and greater clearance and, hence, increasing the instability of the slide on the guide.

Furthermore, since the slide is small-sized, manufacturers cannot fit, on board the slide, different permanent magnets, which are instead necessary in order to generate significant driving forces an, hence, ensure high-level dynamic performances (namely, accelerations).

Document WO0064759 discloses a manufacturing machine provided with at least one pair of opposite welding heads, each arranged on a respective conveyor provided with a linear motor.

Document WO2017108423 describes a linear transport system for holding heads provided with a double track, each track being provided, in turn, with a respective linear motor.

Document EP3038959 discloses a component transporting unit provided with a one-track linear motor and comprising a plurality of holding heads.

DESCRIPTION OF THE INVENTION

The object of the invention is to provide a unit to feed components in an automatic manufacturing machine, which does not suffer from the drawbacks described above and, at the same time, is easy and economic to be manufactured.

According to the invention, there is provided a unit to feed components in an automatic manufacturing machine according to the appended claims.

The appended claims describe preferred embodiments of the invention and form an integral part of the description.

BRIEF DESCRIPTION OF THE DRAWINGS

The invention will now be described with reference to the accompanying drawings, which show some non-limiting embodiments thereof, wherein.

PREFERRED EMBODIMENTS OF THE INVENTION

Figure 1:
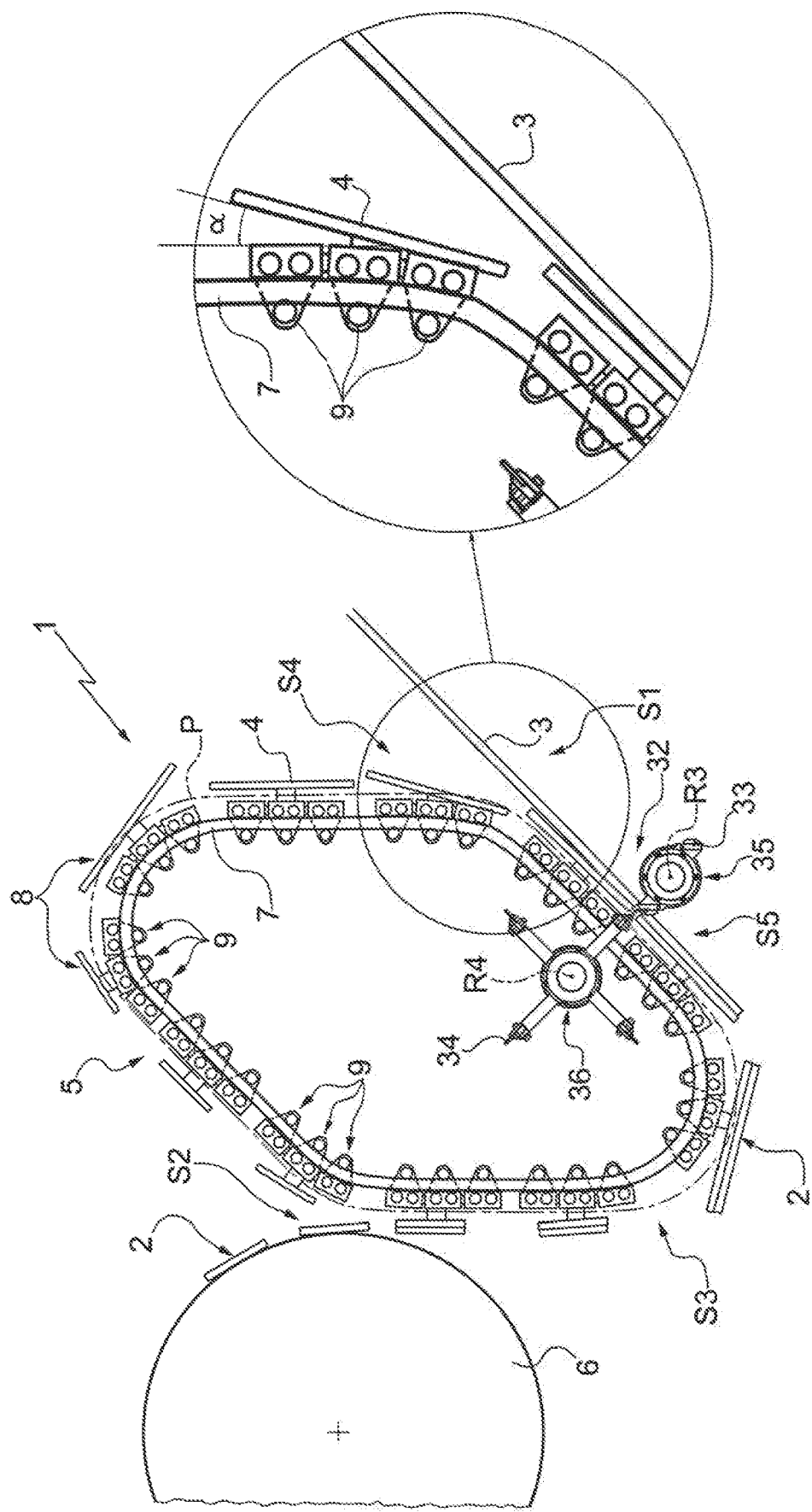
FIG. 1 is a schematic front view of a unit to feed components of hygiene absorbent articles according to the invention.

In FIG. 1, number 1 indicates, as a whole, a feeding unit 1 to feed a component 2 of a hygiene absorbent article. The feeding unit 1 is part of an automatic manufacturing machine to manufacture absorbent hygiene articles.

In the preferred and non-limiting embodiment shown in FIG. 1, each component 2 is obtained from a continuous band 3 (unwound from a reel, which is not shown herein) by means of a crosswise cut of the continuous band 3; namely, the continuous band 3 is cyclically cut crosswise so as to separate, in succession, the single components 2 from the continuous band 3. According to a different embodiment which is not shown herein, the feeding unit 1 singularly receives the components 2, which, hence, are not separated from the continuous band 3.

The feeding unit 1 comprises a plurality of sucking holding heads 4, which are, each, designed to receive and hold a corresponding component 2. Furthermore, the feeding unit 1 comprises a conveyor 5, which supports the sucking holding heads 4 and cyclically moves each sucking holding head 4 along an application path P (shown in FIG. 1).

The application path P goes through an input station S1, where the sucking holding head 4 receives a corresponding component 2, and through an output station S2, where the sucking holding head 4 releases the component 2 to a subsequent device 6. In FIG. 1, the device 6 is represented as a conveyor belt, but it is evident that the device 6 receiving the components 2 in succession in the output station S2 can be any type of device of a manufacturing machine to manufacture hygiene absorbent articles.

Figure 2:
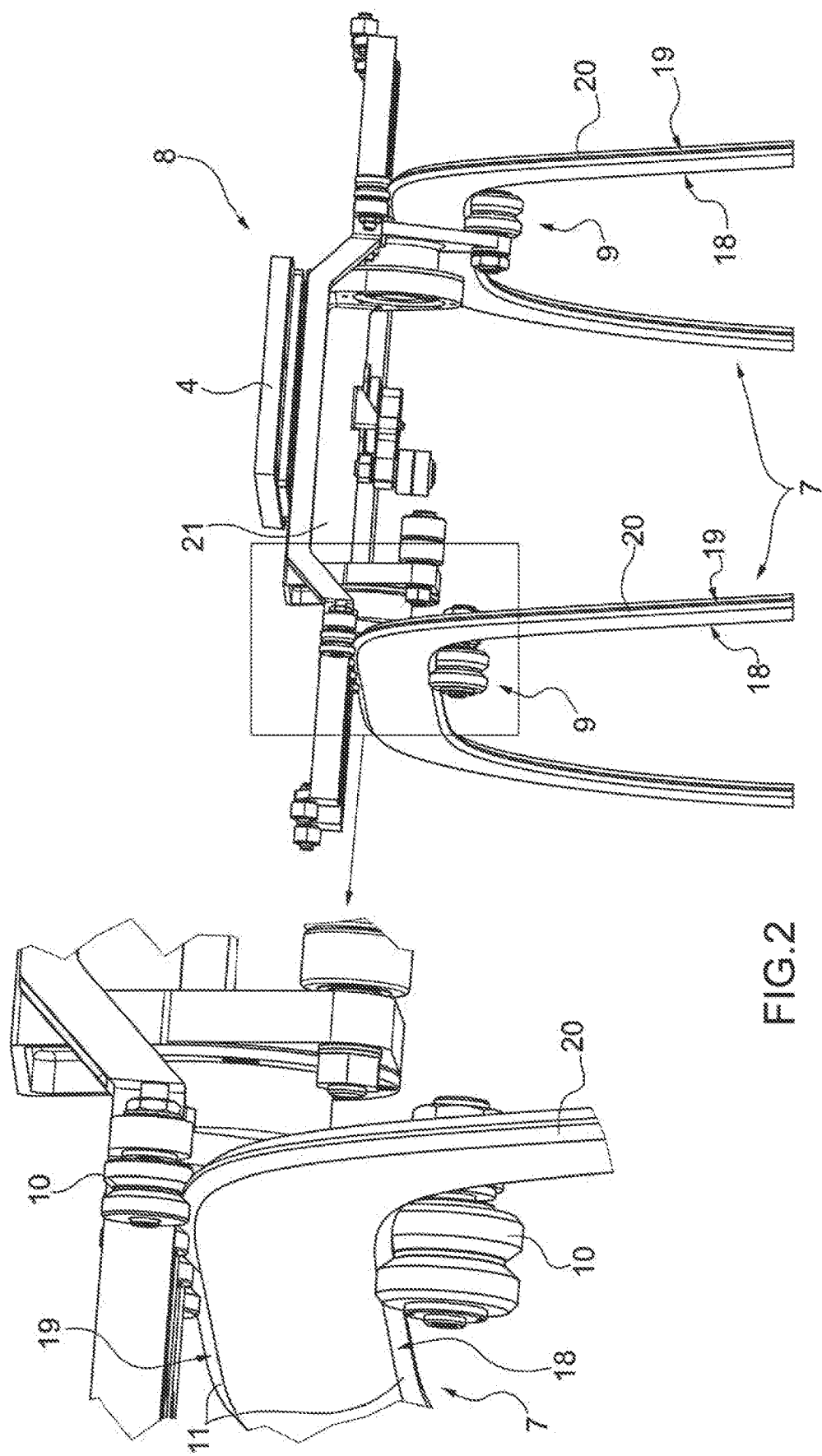
FIG. 2 is a simplified perspective view of part of the feeding unit of FIG. 1, wherein a movable equipment and part of a guide are highlighted

The conveyor 5 comprises a closed curved guide 7 (i.e. closed in a ring shape forming a circuit without a start or an end), which is arranged in a fixed position along the application path P. Furthermore, the conveyor 5 comprises a plurality of equipments 8, each supporting a respective holding head 4 and provided with three slides 9, each coupled to the guide 7 so as to freely slide along the guide 7 by means of a plurality of wheels 10, which are idle on the slide 9 and roll along respective rolling surfaces 11 of the guide 7 (as shown in FIG. 2). According to other embodiments which are not shown herein, each equipment 8 comprises a different number of slides 9 (for example one single slide 9, two slides 9, four slides 9 . . . ).

Figure 3:
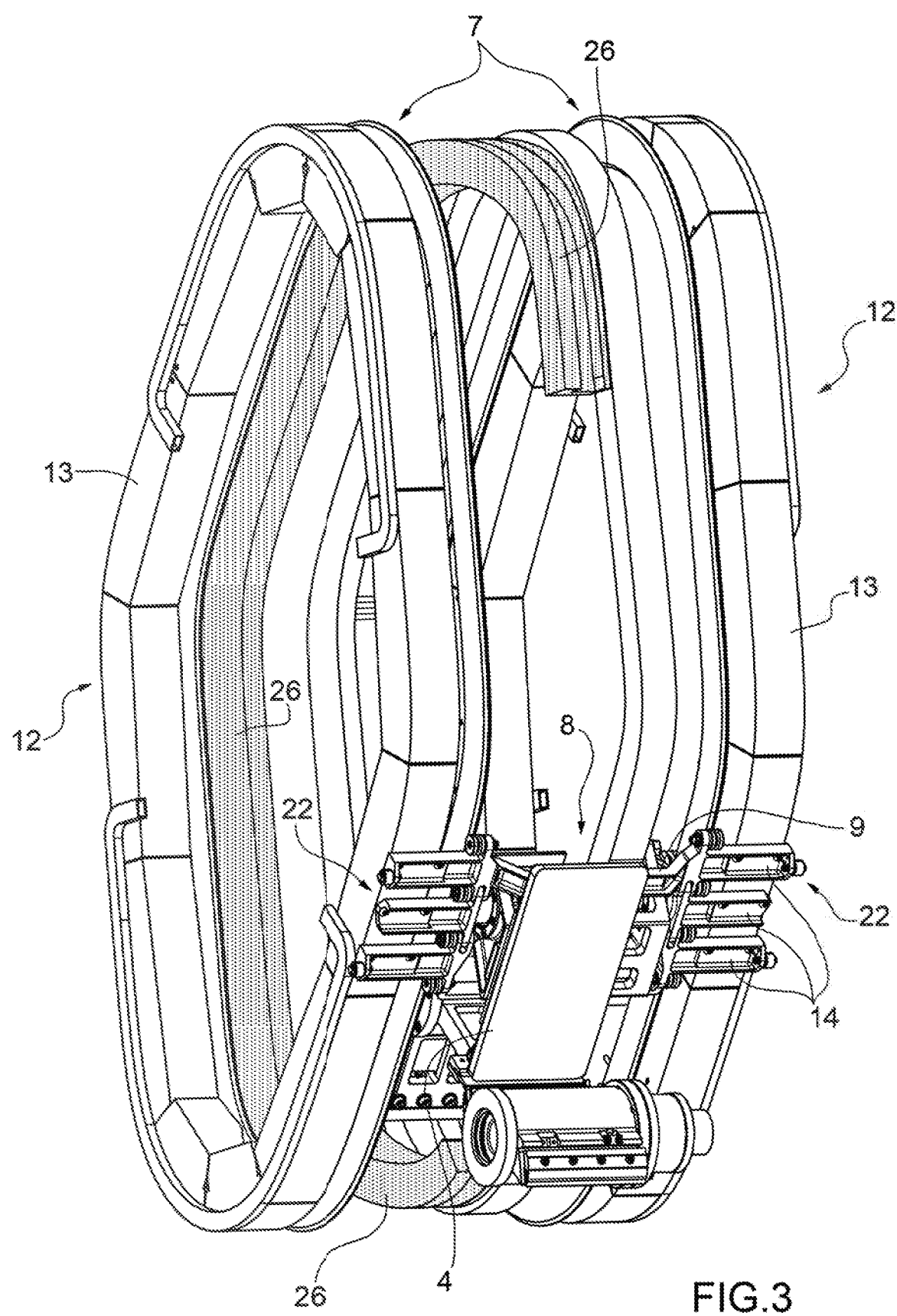
FIG. 3 is a schematic perspective view of the feeding unit of FIG. 1.

Finally, according to FIG. 3, the conveyor 5 comprises a linear electric motor 12, which moves the slides 9 carrying the equipments 8 and, hence, the sucking holding heads 4 along the application path P. The linear electric motor 12 comprises a closed curved stator 13 (i.e. a fixed primary element), which is arranged in a fixed position along the guide 7, and a plurality of movable sliders 14 (i.e. movable secondary elements), each electro-magnetically coupled to the stator 13 so as to receive, from the stator 13, a driving force and rigidly connected to a corresponding slide 9.

Figure 6:
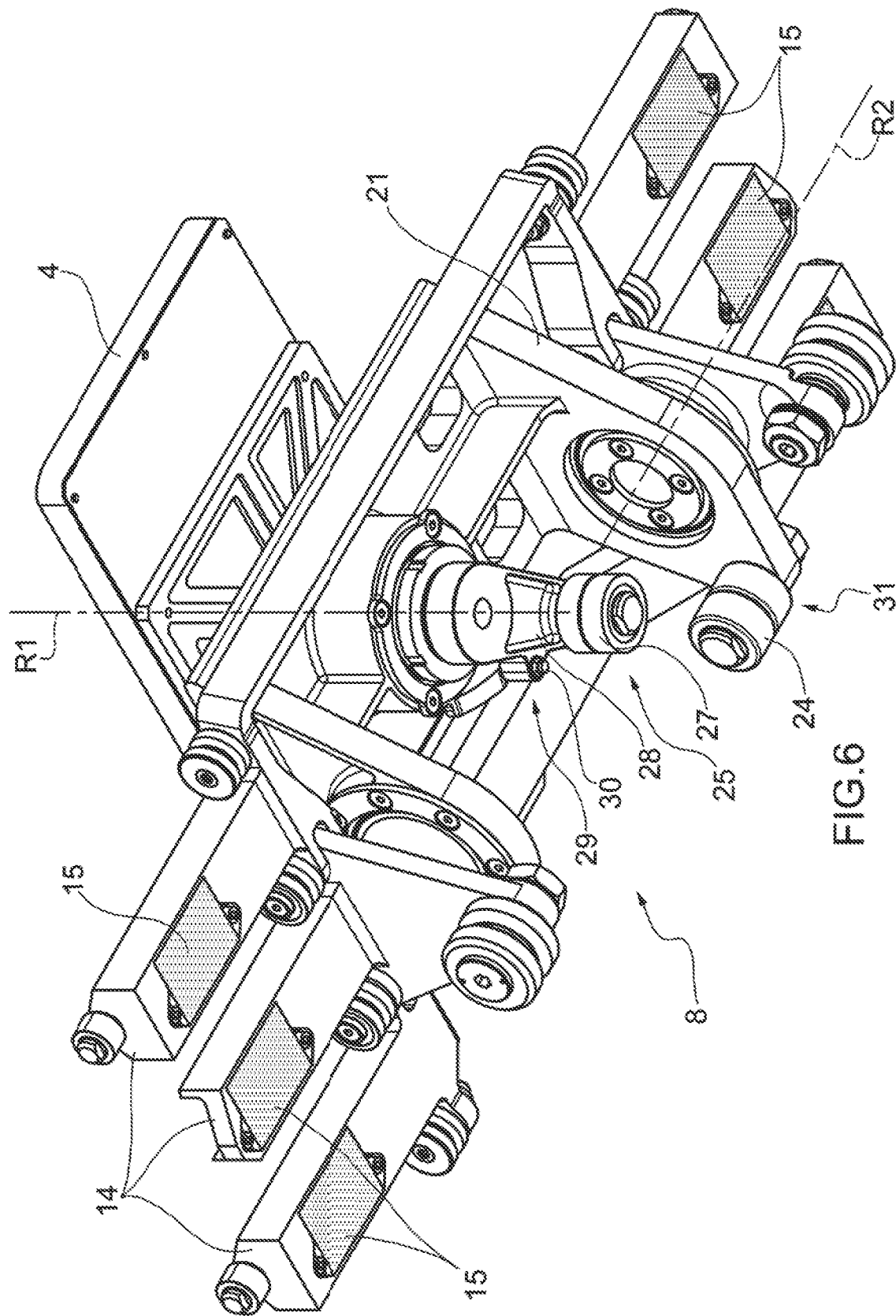

The stator 13 of the linear electric motor 12 comprises a ferromagnetic armature having a series of slots housing windings designed to be run through electric currents variable in time in order to generate corresponding stator magnetic fields (which are variable in time). According to FIG. 6, each slider 14 of the linear electric motor 12 comprises a ferromagnetic armature in which there is arranged at least one permanent magnet 15 generating a rotor magnetic field (which is constant in time) interacting with the stator magnetic field (which is variable in time) in order to generate, on the slider 14, a driving force of electromagnetic origin. In each slide 9, the slider 14 is mounted so as to be very close to the stator 13 (approximately 1-2 millimetres away), so as to minimize the gap existing between the ferromagnetic armature of the slider 14 and the ferromagnetic armature of the stator 13.

A control device is provided, which controls the linear electric motor 12 applying a variable voltage to the windings of the stator 13. The control device preferably uses a closed loop (i.e. feedback) control system to control the position of each slider 14 (hence, of each slide 9). As a consequence, the control device must know, in real time and with a good precision, the actual position of each slider 14 (hence, of each slide 9) along the application path P; to this aim, the control device can track the actual position of each slider 14 along the application path P by means of estimation algorithms based on electrical signals at the ends of the windings of the stator 13 or the control device can receive the detection of a dedicated sensor, which is arranged along the application path P. For example, the position sensor comprises a magnetoresistive material measuring band, which is arranged along the application path P, and, for each slider 12, a corresponding permanent magnet 15, which is arranged close to the measuring band. In other words, along the application path P there is an encoder detection device, which allows the position of each permanent magnet 15 associated with each slider 14 to be detected with precision.

According to FIG. 3, the stator 13 of the linear electric motor 12 is parallel to the guide 7 and adjacent to the guide 7. In other words, the stator 13 of the linear electric motor 12 and the guide 7 are arranged on two parallel planes; in this way, the stator 13 of the linear electric motor 12 can be mechanically connected close to the guide 7.

According to a preferred, though non-binding embodiment, the stator 13 of the linear electric motor 12 is divided into different sectors (twelve in FIG. 3, but there could be more or less of them) arranged one after the other along the guide 7. The single sectors of the stator 13 are mechanically and electrically independent of one another, namely each sector of the stator 13 is electrically powered by a control device of its own, which is exclusively dedicated to its sector (hence, is different and separate from the control devices of the other sectors); obviously, there is a central control unit, which controls the control devices in a coordinated manner so as to move the slides 9 (hence, the corresponding sucking holding heads 4) along the application path P according to a desired law of motion.

Figure 7:
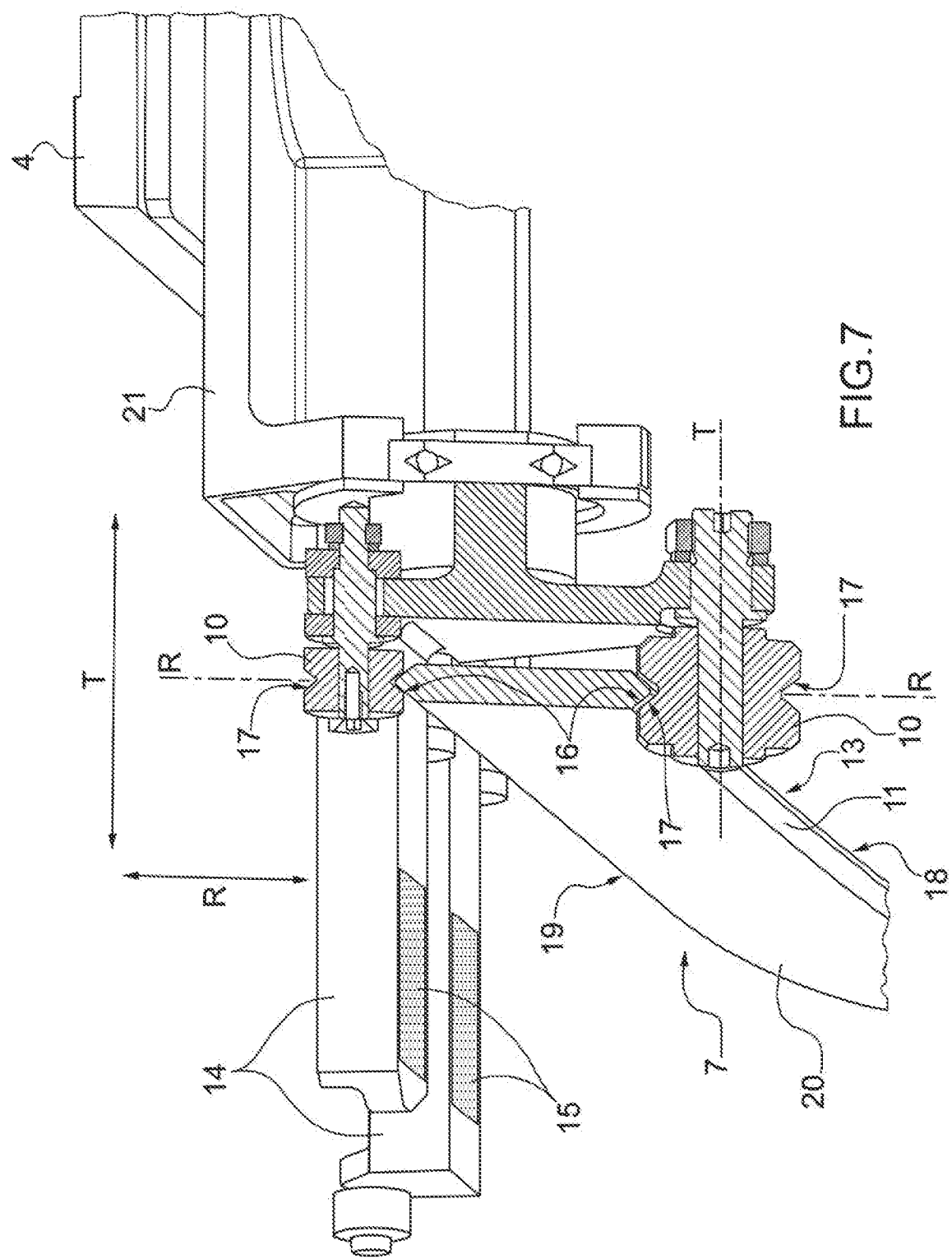
FIG. 7 is a perspective sectional view of part of the feeding unit of FIG. 1 by means of a plane perpendicular to the conveying direction of a movable equipment.

According to FIG. 7, the guide 7 has, on the rolling surfaces 11, a transverse profile 16 having a concavity or a convexity. The wheels 10 have, on the surface in contact with the guide 7, a transverse profile 17, which has a convexity or a concavity, which is complementary to the profile 16 (namely, when the profile 16 is convex, the corresponding profile 17 is concave and vice versa). The profile 17 generates, with the profile 16, a shape coupling between the guide 7 and the wheels 10, which prevents the slide 9 from moving crosswise relative to the guide 7. In other words, the shape coupling generated between the transverse profile 16 of the guide 7 and the transverse profile 17 of each wheel 10 prevents the slide 9 from moving along a direction T which is transverse to the guide 7, so as to also prevent the slide 9 from derailing out of the guide 7.

Advantageously, though not necessarily, the profile 16 and the profile 17 are "V"-shaped. In this way, thanks to the presence of the vertex in the "V" shape, a high precision of the application path P followed by the wheels is ensured.

According to a preferred, though non-limiting embodiment shown in FIGS. 1, 2, 7, 9 and 10, each slide 9 has at least one pair of opposite wheels 10, which are coupled to a side 18 and to a side 19, respectively, of the guide 7 (which are opposite one another), thus forbidding the movement of the slide 9 relative to the guide 7 along a direction R (shown in FIG. 7), which is radial to the application path P. In the preferred, though non-limiting embodiment shown in FIGS. 1, 2, 7, 9 and 10, each slide 9 has three wheels 10: two smaller wheels 10, which slide along the side 19 of the guide 7, and a larger wheel 10, which slides along the side 18 of the guide 7.

According to a preferred, though non-limiting embodiment shown in FIG. 2, the guide 7 comprises two tracks 20, which are parallel to one another and spaced apart from one another. As a consequence, the equipment 8 comprises two groups of opposite slides 9 (each group for each track 20) and a connection element 21, which connects the two groups of slides 9 to one another and supports the holding head 4.

Figure 4:
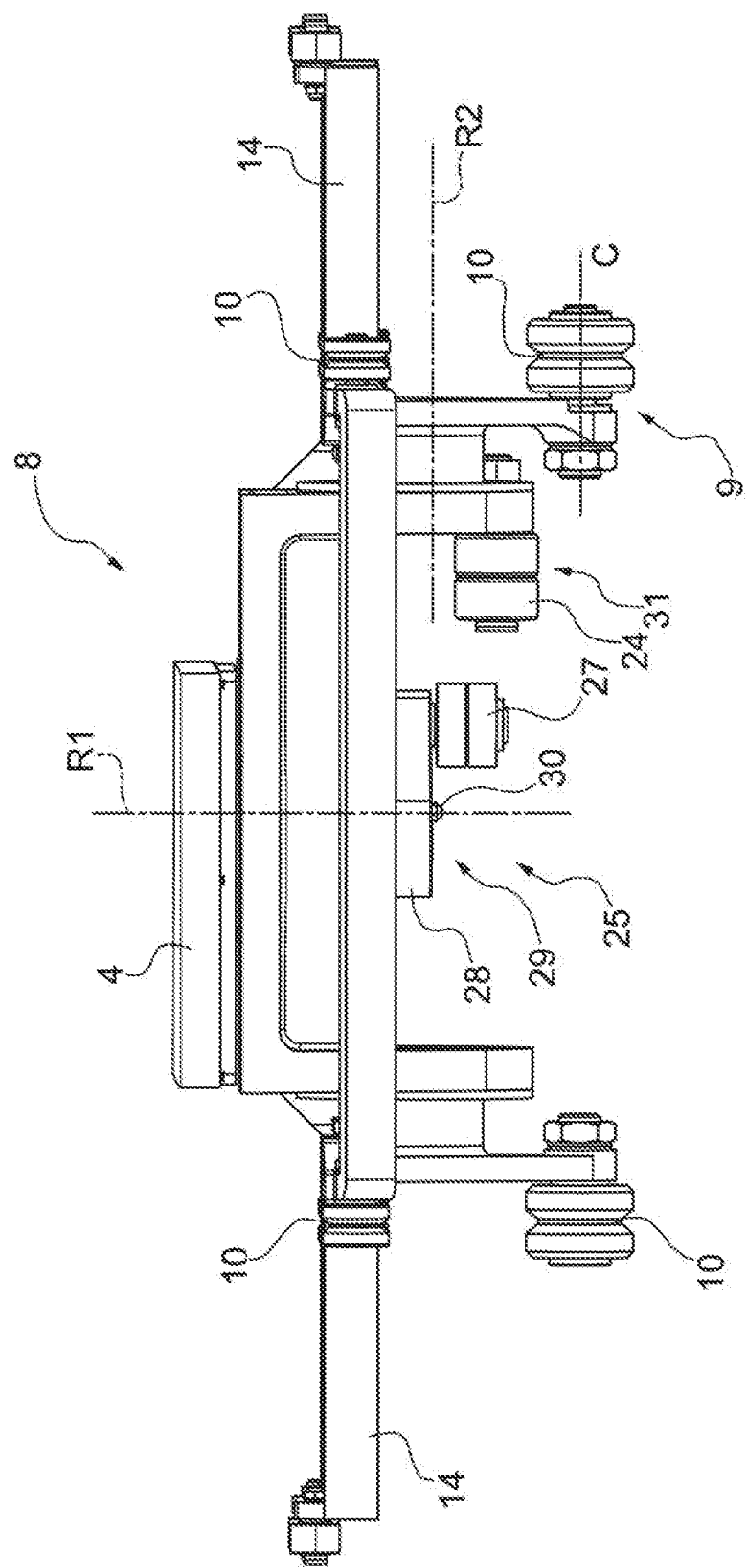
FIG. 4 is a side view of a movable equipment of the feeding unit of FIG. 1.
Figure 8:
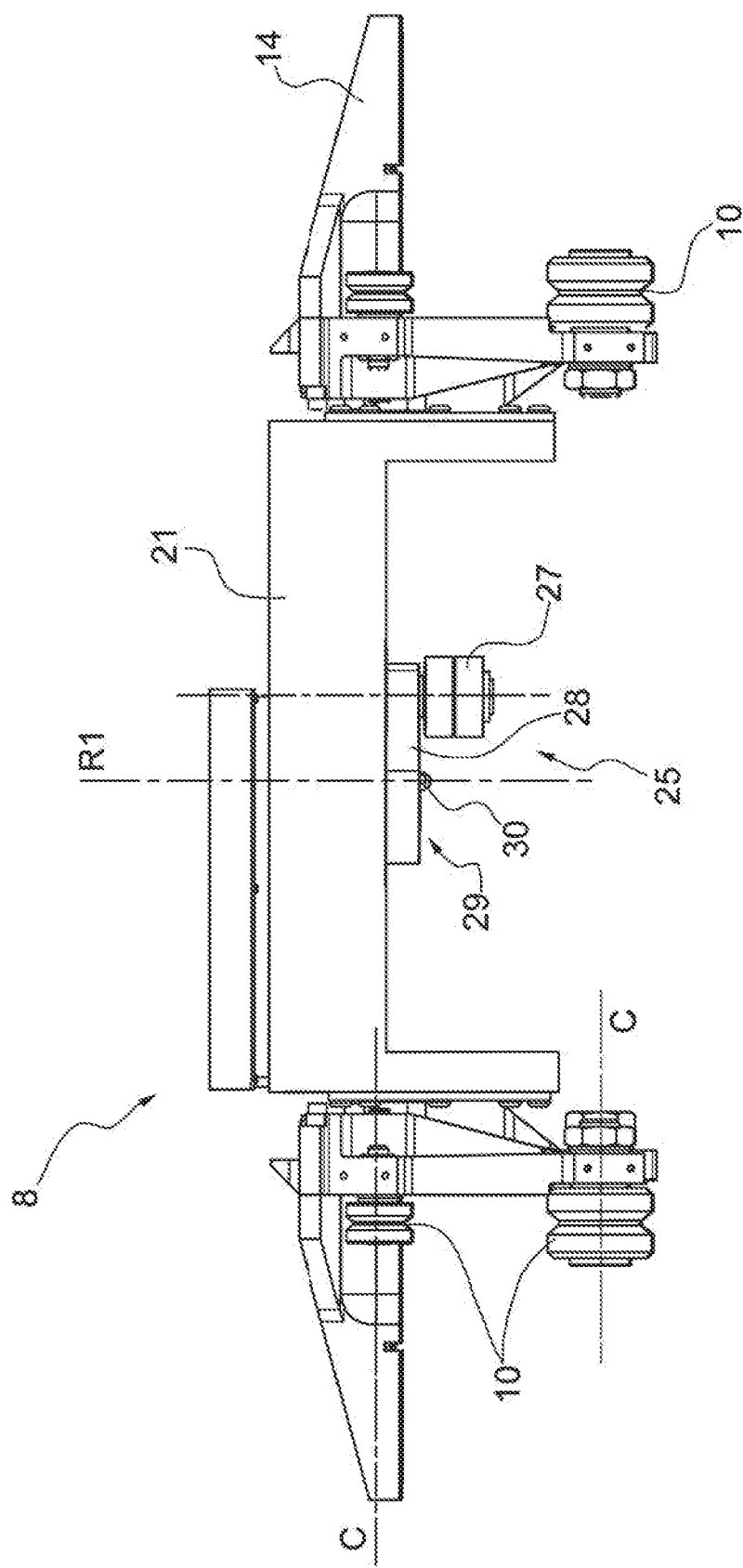
FIG. 8 is a side view of a different embodiment of the movable equipment of FIG. 4.

According to FIGS. 4 and 8, advantageously, in each equipment 9 the wheels 10 of one of the slides 9 are floating relative to the corresponding slide 9 along a compensation direction C, which is transverse to the application path P. By so doing, building and/or assembling imperfections, which unavoidably arise in the parallel arrangement and in the uniform character of the two tracks 20, can be solved.

Figure 9:
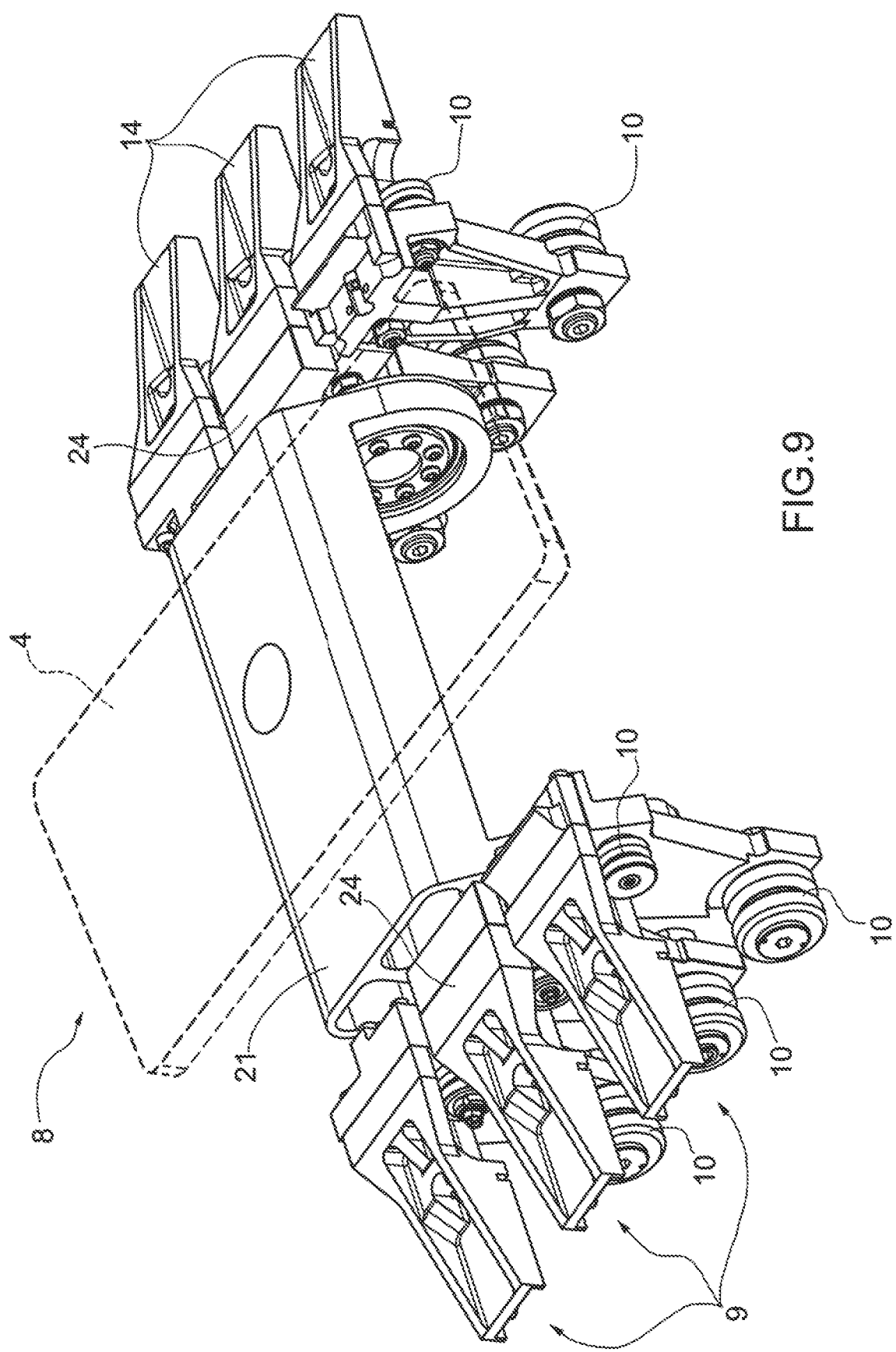
FIGS. 9 and 10 are an upper perspective view and a lower perspective view, respectively, of the movable equipment of FIG. 8.
Figure 10:
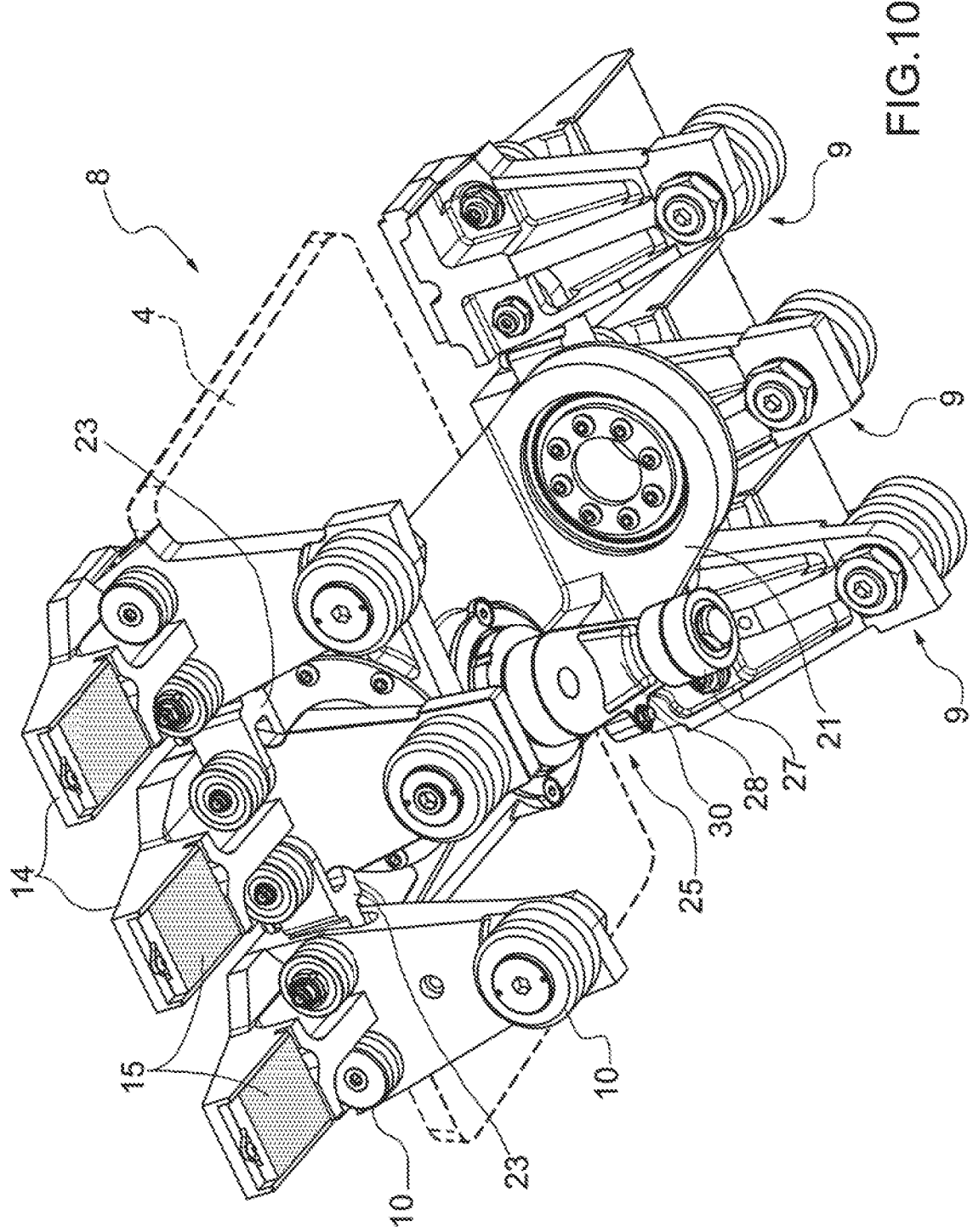

According to a preferred, though non-limiting embodiment shown, for example, in FIGS. 8, 9 and 10, each slide 9 is provided with three wheels 10. In particular two (smaller) wheels 10 slide on the outer rolling surface 11 of the guide 7, namely along the side 19 of the guide 7, whereas one single (larger) wheel 10 slides on the inner rolling surface 11 of the guide 7, namely along the side 18 of the guide 7. In this way, the (larger) wheel 10 sliding along the side 18 of the guide 7 forms, with the two (smaller) wheels 10 sliding along the side 19 of the guide 7, two pairs of wheels 10, one with each one of the (smaller) wheels 10 sliding along the side 19 of the guide 7.

Advantageously, though not necessarily, each equipment 8 comprises two trains 22 of slides 9, each comprising three slides 9 which slide one the same track 20 (alternatively, each train 22 of slides 9 could comprise only one/two slides 9 or four/five slides 9). Furthermore, the connection element 21 connects at least one slide 9 sliding on a track 20 and another slide 9 sliding on the other track 20 to one another.

Figure 5:
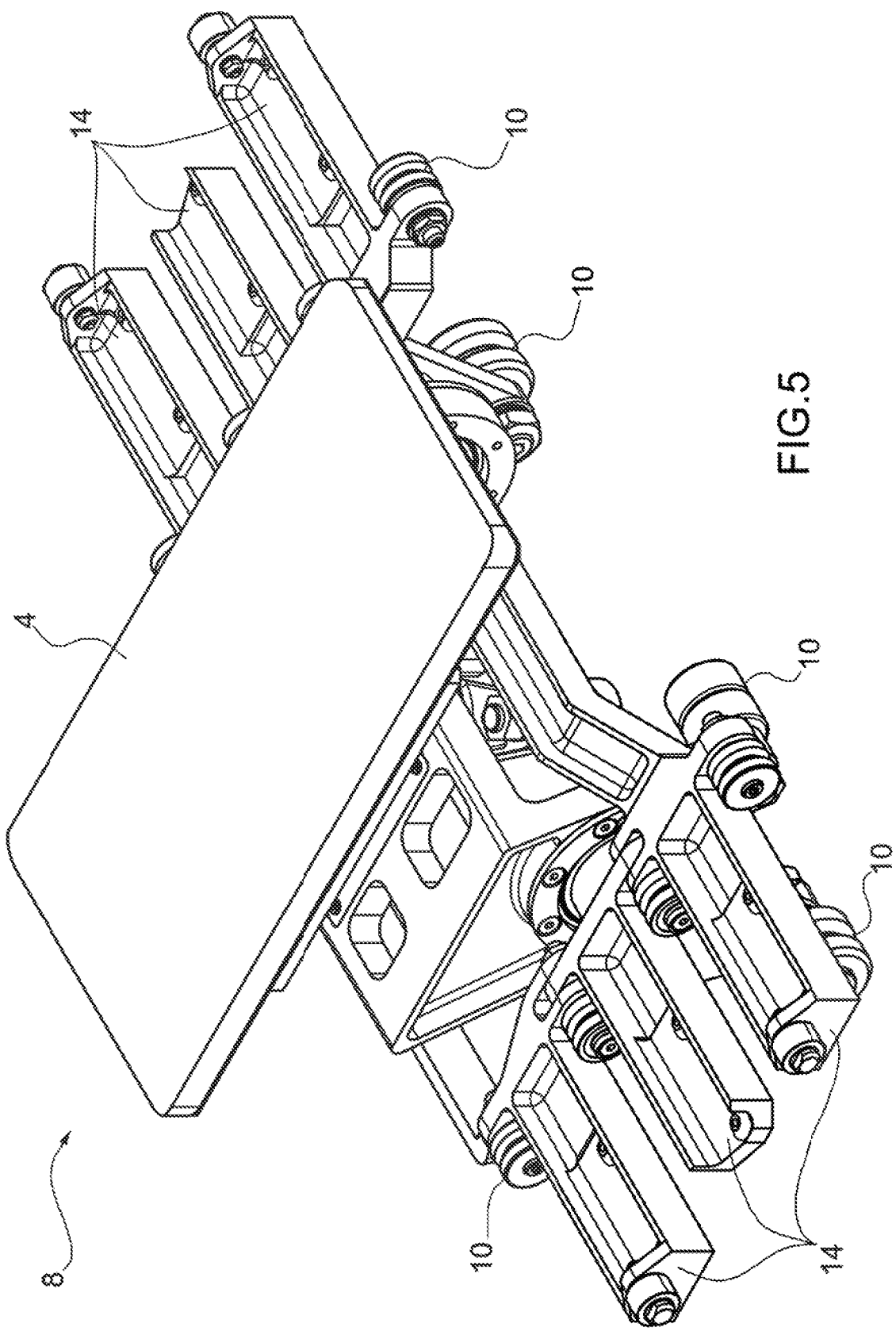
FIGS. 5 and 6 are an upper perspective view and a lower perspective view, respectively, of the movable equipment of FIG. 4.

Two slides 9 sliding on the same track 20 are connected in an articulated manner by means of a fork (FIG. 5) or by means of a connecting rod 23 (having a fork at one of the ends and shown in FIG. 10), which permit a relative rotation of the two slides 9 sliding on the same track 20 along the curved segments of the guide 7.

According to a preferred embodiment, each equipment 8 comprises two trains 22 of slides 9, each comprising three slides 9, which slide on a same track 20. Furthermore, the connection element 21 connects the sole central slide 9 of a train 22 to the sole central slide 9 of the other train. According to a further preferred embodiment of the invention, the floating wheels 10 are present only on the slide 9 arranged at the centre (namely, arranged between the two side slides 9). This is due to the fact that, as far as the side slides 9 (arranged on opposite sides of the central slide 9) are concerned, the function of compensation of the parallel arrangement and of possible lacks of homogeneity between the different tracks 20 is fulfilled (enabled) by the connecting rod 23 connecting the two side slides 9 to the central slide 9.

According to a preferred, though non-limiting embodiment shown in FIG. 1, the feeding unit 1 comprises a rotation station S3, which is arranged along the feeding path P and where each holding head 4 makes a rotation relative to the equipment 8 and around a rotation axis R1 (shown in FIGS. 4 and 8) in order to change the orientation of the component 2. In particular, each sucking holding head 4 is mounted in a rotary manner on the equipment 8 so as to rotate around the rotation axis R1 and there is a cam operating system 25 to control the rotation of the sucking holding head 4 around the rotation axis R1.

According to FIGS. 3, 4 and 8, the cam operating system 25 comprises a cam 26 (shown in FIG. 3), which is arranged in a fixed position beside the guide 7 and along the application path P, and, for each holding head 4, at least one corresponding cam follower roller 27 (shown in FIGS. 4 and 8), which is coupled to the cam 26 (namely, slides on the cam 26 so as to follow the profile of the cam 26) and is mechanically connected to the sucking holding head 4.

According to a preferred non-limiting embodiment (shown in FIGS. 4 and 8), in each equipment 8 the cam follower roller 27 is oriented parallel to the rotation axis R1; further optimizations are possible by causing the axis R1 and the symmetry axis of the cam follower roller 27 to converge in a suitable point; furthermore, there is an operating arm 28 having a first end, on which there is mounted, in a rotary manner, the roller 27, and a second end, which is angularly integral to the sucking holding head 4. In this embodiment, an end of each operating arm 28 is directly constrained to a shaft supporting the sucking holding head 4, so that the rotary movement of the operating arm 28 becomes a same rotary movement of the sucking holding head 4.

According to a further embodiment shown in FIG. 3, the cam 26 is interrupted along a portion of the application path P, so as to permit the introduction of stations, interfering in terms of space, along the application path P (such as, for example, a cutting station). In this embodiment, a locking device 29 (shown in FIGS. 4 and 8) is provided, which prevents the holding head 4 from rotating around the rotation axis R1, so as to avoid accidental rotations of the holding head 4 along the segment where the cam 26 is interrupted.

Furthermore, a control device is provided, which activates the locking device 29 upstream of the portion of the application path P where the cam 26 is interrupted and deactivates the locking device 29 downstream of the portion of the application path P where the cam 26 is interrupted. In other words, the locking device 29 shifts from an active (locking) position, in which the locking device 29 prevents the holding head 4 from rotating around the rotation axis R1, to a passive (release) position, in which the locking device 29 allows the holding head 4 to freely rotate controlled by the cam 26 by means of the cam follower roller 27.

According to a possible embodiment, the locking device 29 comprises a locking pin 30, which can axially slide between an active position and a passive position. Furthermore, the control device comprises an elastic element, which pushes the locking pin 30 towards the active position, and an actuator element (not shown), which pushes the locking pin 30 towards the passive position, thus compressing the elastic element. According to a preferred, though non-limiting embodiment of the invention, the locking pin 30 is made of a ferromagnetic material and the actuator element consists of a magnet (not shown), which magnetically attracts the locking pin 30 towards the passive position.

According to a further embodiment, the feeding unit 1 comprises a rotation station S4, which is arranged along the feeding path P (FIG. 1) and in which the holding head 4 makes a rotation relative to the equipment 8 and around a rotation axis R2 (shown in FIGS. 4 and 6), which is transverse to the feeding path P, so as to change the inclination of the holding head 4. In this way, the angle α (shown in FIG. 1) existing between each holding head 4 and the guide 7 can be changed in order to allow the holding head 4 to approach the continuous band 3 in an ideal manner.

In particular, the rotation around the rotation axis R2 takes place by means of a further cam operating system 31, which is completely similar to the operating system 25. As a consequence, the further operating system 31 also comprises a cam follower roller 24 (shown, for example, in FIGS. 4 and 6) and a cam (nor shown), on which the cam follower roller 24 slides.

According to a preferred non-limiting embodiment, as already mentioned above and according to FIG. 1, in the input station S1 the holding head 4 receives a corresponding component 2 connected, without gaps, to a continuous band 3; furthermore, there is a cutting station S5, which is arranged along the application path P downstream of the input station S1 and is provided with a cutting device 32, which cuts the continuous band 3 crosswise so as to separate the component 2 held by the holding head 4 from the remaining part of the continuous band 3. In other words, when, in the input station S1, a component 2 is engaged by a corresponding sucking holding head 4, the component 2 is still part of the continuous band 3 (namely, is connected without gaps to the continuous band 3) and is separated from the continuous band 3 by means of crosswise cut in the cutting station S5 arranged downstream of the input station S1.

According to a further non-limiting embodiment, upstream of the input station S1 (hence, since the guide 7 is closed, between the output station S2 and the input station S1) there is the second rotation station S4, which allows the holding head 4 to rotate around the rotation axis R2 in order to change the angle α and, hence, help the holding head approach the band 3, preventing a (sharp) end of the holding head 4 from touching the band 3, damaging it, before the holding head 4 is parallel to the band 3.

According to a preferred, though non-binding embodiment, between the cutting station S5 and the output station S2 (namely, downstream of the cutting station S5 and upstream of the output station S) there is the rotation station S3, where each sucking holding head 4 rotates by 90° (or, alternatively, by any other angle other than 90°) relative to the conveyor 5 and around the rotation axis R1 (shown in FIG. 4), which is arranged radially (namely, perpendicularly) to the application path P.

In particular, the cutting device 32 comprises: at least one blade 33 and at least one counter-blade 34, which cooperate with one another to cut the continuous band 3 crosswise; a cutting drum 35, which is arranged on a side of the application path P, supports the blade 33 and rotates around a rotation axis R3 so as to cyclically allow the blade 33 to come into contact with the continuous band 3; and a counter-drum 36, which is arranged on a side of the application path P opposite the cutting drum 35, supports the counter-blade 34 and rotates around a rotation axis R4 (parallel to the rotation axis R3) so as to cyclically allow the counter-blade 34 to come into contact with the continuous band 3 on the opposite side of the blade 33.

The number of blades 33 supported by the cutting drum 35 is completely independent of and variable relative to the number of counter-blades 34 supported by the counter-drum 36, since the control units of the aforesaid drums 35 and 36 are free to control them with different speeds, provided that the rhythm of contact with the band 3 is synchronous.

Figure 11:
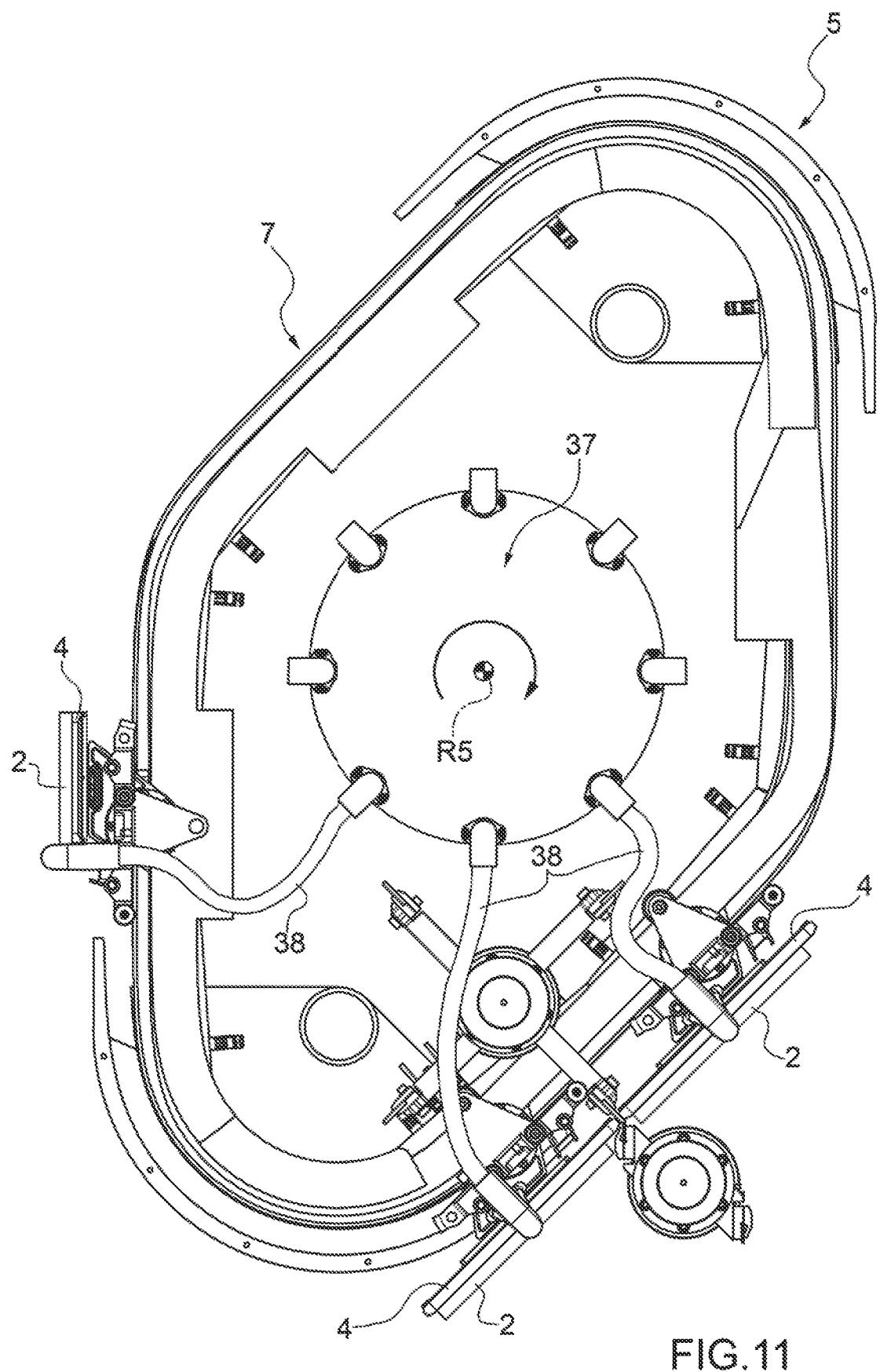
FIG. 11 is a schematic front view of the feeding unit of FIG. 1 with, highlighted, a rotary vacuum chamber connected to the movable equipments in a pneumatic manner.

According to a preferred, though non-limiting embodiment shown in FIG. 11, the unit 1 comprises a drum, which is mounted so as to rotate around a rotation axis R5 and inside which there is defined a suction chamber 37 (with a preferably cylindrical shape), which is connected in a pneumatic manner to the holding heads 4 present on the single equipments 8 by means of a flexible connection system in order to transmit a suction, namely a negative pressure relative to the room pressure, and, hence, allows the holding heads 4 to attract and hold the components 2 through suction.

The flexible connection system comprises, for each equipment 8 (namely, for each holding head 4), a corresponding flexible (articulated) hose 38, in particular made of plastic, which connects the equipment 8 (carrying a corresponding holding head 4) to the suction chamber 37 in a pneumatic manner. In order to prevent the flexible hoses 38 from intertwining and breaking due to the cyclical movement of the equipments 8, the suction chamber 37 can rotate (together with the corresponding drum) around the rotation axis R5 (corresponding to the symmetry axis of the cylindrical suction chamber 37). In other words, the suction chamber 37 rotates around the rotation axis R5 in a manner which, on average, is synchronous with the sliding of the equipments 8 along the guide 7, so as to prevent the flexible hoses 38 from intertwining and breaking In other words, the suction chamber 37 rotates around the rotation axis R5 with a rotation speed which is equal to the mean speed of the equipments 8 along a complete lap of the guide 7. Obviously, the suction chamber 37 cannot follow the movement of each equipment 8 point by point (namely, instant by instant) and, therefore, there are moments in which the suction chamber 37 is in advance or in delay relative to each equipment 8; these cyclical variations ("pulsations") of the distance between the suction chamber 37 and each equipment 8 are compensated by elastic deformations of the corresponding flexible hoses 38.

According to an embodiment, the rotation axis R5 is arranged in the area of the centre of gravity of the guide 7 so as to minimize the extent of the cyclical variations ("pulsations") of the distance between the suction chamber 37 and each equipment 8. In particular, it is evident that the variation of the distance between the suction chamber 37 and the single equipment 8 is due both to a geometric factor deriving from the relationship between the shapes of the guide 7 and the suction chamber 37, respectively, and to the law of motion with which the equipments move along the guide.

According to a possible non-limiting embodiment, the suction chamber 37 rotates at a rotation speed that is variable in time and is equal, instant by instant, to the mean of the instantaneous speeds of the equipments 8 running along the guide 7. According to an alternative non-limiting embodiment, the suction chamber 37 rotates at a rotation speed that is constant in time and is equal to the mean speed of the equipments 8 along a complete lap of the guide 7.

The embodiments described herein can be combined with one another, without for this reason going beyond the scope of protection of the invention.

In the preferred embodiment show in the accompanying figures, the feeding unit 1 described above is used in an automatic manufacturing machine to manufacture hygiene absorbent articles. According to other embodiments which are not shown herein, the feeding unit 1 described above can be used in other types of automatic manufacturing machines manufacturing products that are (even completely) different from hygiene absorbent articles; for example, the feeding unit 1 described above could be used in an automatic manufacturing machine for the production of food or in an automatic manufacturing machine to process products of the tobacco industry (for example, in a unit for forming groups of cigarettes).

The feeding unit 1 described above has numerous advantages.

First of all, the feeding unit 1 described above can stand fast production rates, as the structure of the slides 9, which is completely symmetrical relative to a plane that is parallel to and equally spaced apart from the tracks 20 of the guide 7, determines a reduced and uniform wear of the wheels 10.

Furthermore, the feeding unit 1 described above allows the components 2 to be moved with very high speeds and accelerations (hence, with fast production rates) thanks to the fact that each movable equipment 8 can be provided with a plurality of sliders 14, which, as a whole, are capable of generating a significant driving force.

LIST OF THE REFERENCE NUMBERS OF THE FIGURES 1 unit
2 component
3 band
4 holding head
5 conveyor
6 device
7 guide
8 equipment
9 slide
10 wheels
11 rolling surfaces
12 linear electric motor
13 stator
14 movable slider
15 magnet
16 first transverse profile
17 second transverse profile
18 first side of the guide
19 second side of the guide
20 track
21 connection elements
22 trains
23 connecting rod
24 cam follower roller
25 operating system
26 cam
27 cam follower roller
28 operating arm
29 locking device
30 locking pin
31 further operating system
32 cutting device
33 blade
34 counter-blade
35 cutting drum
36 counter-drum
37 suction chamber
38 flexible hoses
P application path
R direction radial to the path
T direction transverse to the path
C transverse compensation direction
S1 input station
S2 output station
S3 first rotation station
S4 second rotation station
S5 cutting station
R1 first rotation axis
R2 second rotation axis
R3 third rotation axis
R4 fourth rotation axis
R5 fifth rotation axis

The invention claimed is:

1. A feeding unit to feed a component in an automatic manufacturing machine; the feeding unit comprising:
at least one holding head, which is designed to receive and hold the component;
a conveyor to cyclically move the holding head along an application path;
an input station, which is arranged along the application path and in which the holding head receives the component;
a first rotation station, which is arranged along the feeding path;
an operating system; and
an output station, which is arranged along the application path downstream of the input station and in which the holding head releases the component;
wherein the conveyor comprises:
a closed curve guide, which is arranged in a fixed position along the application path;
an equipment, supporting the holding head and provided with at least one slide coupled to the guide so as to freely slide along the guide by means of a plurality of wheels, which are idle on the slide and roll along respective rolling surfaces of the guide, wherein the holding head is fitted on the equipment in a rotary manner, so as to rotate around a first rotation axis; and
a linear electric motor, which comprises a stator arranged in a fixed position along the guide, and a movable slider electro-magnetically coupled to the stator so as to receive, from the stator, a driving force and rigidly connected to the slide,
wherein at the first rotation station, the holding head rotates relative to the equipment and around the first rotation axis so as to vary the orientation of the component;
wherein the operating system controls the rotation of the holding head around the first rotation axis and comprises:
a cam, which is arranged in a fixed position beside the guide and along the application path, wherein the cam is interrupted along a portion of the application path,
at least one cam follower roller, which can be coupled to the cam and is mechanically connected to the holding head,
a locking device which prevents the holding head from rotating around the first rotation axis, and
a control device which activates the locking device upstream of the portion of the application path where the cam is interrupted and deactivates the locking device downstream of the portion of the application path where the cam is interrupted;
wherein the guide has, in the area of the rolling surfaces, a first transverse profile having a concavity or a convexity;
wherein the wheels have, on the surface in contact with the guide, a second transverse profile, which has a convexity or a concavity, is complementary to the first profile, and generates, with the first profile, a shape coupling between the guide and the wheels, which forbids a transverse movement of the slide relative to the guide;
wherein the slide has at least one pair of opposite wheels, which are respectively coupled to a first side and to a second side of the guide, which are opposite one another, thus forbidding the movement of the slide relative to the guide along a direction, which is radial to the application path;

wherein the guide comprises at least two tracks, which are parallel to and spaced apart from one another;

wherein the equipment comprises at least one pair of opposite slides and a connection element, which connects the two slides to one another and supports the holding head; and wherein at least one of the pairs of opposite wheels available on one of the two slides of the equipment is floating relative to the slide along a compensation direction, which is transverse to the application path.

2. The feeding unit according to claim 1, wherein the first profile and the second profile are "V"-shaped.

3. The feeding unit according to claim 1, wherein:

the equipment comprises at least two trains of slides, each comprising at least one slide, which slides on a same track; and the connection element connects at least one slide sliding on a track and another slide sliding on the other track to one another.

4. The feeding unit according to claim 3, wherein:

the equipment comprises two trains of slides, each comprising three slides, which slide on a same track; and the connection element connects the sole central slide of a train to the sole central slide of the other train.

5. The feeding unit according to claim 1, wherein:

the locking device comprises a locking pin, which can axially slide between an active position and a passive position; and the control device comprises an elastic element, which pushes the locking pin towards the active position, and an actuator element, which pushes the locking pin towards the passive position, thus compressing the elastic element.

6. The feeding unit according to claim 5, wherein:

the locking pin is made of ferromagnetic material; and the actuator element consists of a magnet, which magnetically attracts the locking pin towards the passive position.

7. The feeding unit according to claim 1, further comprising a second rotation station, which is arranged along the feeding path and in which the holding head rotates relative to the equipment and around a second rotation axis, which is transverse to the feeding path, so as to vary the inclination of the holding head.

8. The feeding unit according to claim 1, wherein:

in the input station, the holding head receives a corresponding component, which is connected—without gaps—to a continuous band; and a cutting station is provided, which is arranged along the application path downstream of the input station and is provided with a cutting device, which cuts the continuous band crosswise, so as to separate the component held by the holding head from the remaining part of the continuous band.

9. The feeding unit according to claim 8, wherein the cutting device comprises:

at least one blade and at least one counter-blade cooperating with one another so as to cut the continuous band crosswise;

a cutting drum, which is arranged on one side of the application path, supports the blade, and rotates around a third rotation axis so as cyclically allow the blade to come into contact with the continuous band, and a counter-drum, which is arranged on one side of the application path opposite the cutting drum, supports the counter-blade, and rotates around a fourth rotation axis so as cyclically allow the counter-blade to come into contact with the continuous band on the opposite side of the blade.

10. The feeding unit according to claim 9, further comprising:

a suction chamber, which is arranged in a central area of the guide and is mounted so as to rotate around a fifth rotation axis; and a flexible connection system, which pneumatically connects the suction chamber to the holding head.

* * * * *